(12) United States Patent
Severino

(10) Patent No.: US 6,918,897 B2
(45) Date of Patent: Jul. 19, 2005

(54) SPF VENDING MACHINE AND METHOD

(76) Inventor: Joseph Severino, 809 Cotswold Rd., Somerdale, NJ (US) 08083

( * ) Notice: Subject to any disclaimer, the term of this patent is extended or adjusted under 35 U.S.C. 154(b) by 441 days.

(21) Appl. No.: 10/210,652

(22) Filed: Jul. 31, 2002

(65) Prior Publication Data

US 2003/0024946 A1 Feb. 6, 2003

Related U.S. Application Data

(60) Provisional application No. 60/309,226, filed on Jul. 31, 2001.

(51) Int. Cl.[7] .............................................. A61M 35/00
(52) U.S. Cl. ........................................................ 604/289
(58) Field of Search ............................ 222/2; 604/289; 132/333; 4/900

(56) References Cited

U.S. PATENT DOCUMENTS

| | | | |
|---|---|---|---|
| 1,982,509 A | * 11/1934 | Frank | .......................... 604/289 |
| 5,460,192 A | 10/1995 | McClain | |
| 5,664,593 A | 9/1997 | McClain | |
| 5,815,995 A | 10/1998 | Adam | |
| 6,142,170 A | * 11/2000 | Belfer et al. | ................. 222/148 |
| 6,302,122 B1 | 10/2001 | Parker et al. | |
| 6,365,986 B1 | 4/2002 | Nonome | |
| 6,367,658 B1 | 4/2002 | Kenney et al. | |
| 6,367,696 B1 | 4/2002 | Inamitsu et al. | |
| 6,382,003 B1 | 5/2002 | Watanuki et al. | |
| 6,387,081 B1 | * 5/2002 | Cooper | ........................ 604/289 |
| 6,470,512 B1 | * 10/2002 | Lau et al. | ...................... 4/900 |
| 2002/0096186 A1 | * 7/2002 | Von Halem | .................. 132/333 |

* cited by examiner

Primary Examiner—Philippe Derakshani
(74) Attorney, Agent, or Firm—Michael B. Fein; Brian L. Belles; Cozen O'Connor P.C.

(57) ABSTRACT

An automatic sunscreen application vending apparatus which accepts payment from a user, stores a plurality of grades of sunscreen lotion, allows the user to select a grade of suntan lotion such as by SPF factor, and sprays the user with the selected grade of stored sunscreen lotion after acceptance of payment.

19 Claims, 6 Drawing Sheets

SPF VENDING MACHINE AND METHOD

This application claims benefit of 60/309,226 filed Jul. 31, 2001.

BACKGROUND OF THE INVENTION

The present invention relates generally to the field of protecting people from the negative effects of ultra-violate rays, and specifically to methods and apparatus for applying sunscreen lotion to the body of a user.

The cosmetic and health-related dangers of being exposed to the ultra-violet ("UV") rays found in sunlight have become a major concern of people worldwide. Among the negative effects resulting from UV ray exposure are skin cancer and increased "wrinkling" of the skin. Despite these dangerous and unwanted consequences, people continue to frequent beaches, pools, and resorts where they tend to spend substantial portions of their days exposed to the direct sunlight. One very common way in which people protect themselves from the harmful effects of the sun is to apply sunscreen lotion to their skin. Sunscreen contains compositions that shield the wearer's skin from the UV rays contained in sunlight. Thus, applying sunscreen to the skin allows the user to spend his or her day in the direct sunlight while minimizing the risk of the negative effects associated with such exposure.

The amount of UV ray protection that a sunscreen lotion provides to a user depends on a number of variables, such as frequency of application, the amount of sunscreen lotion applied per application, and the particular sun protection factor ("SPF") of the sunscreen lotion being used. Sunscreen lotions come in various grades having SPF ratings, the most common of which vary from 2 to 45. The higher the SPF factor of a sunscreen lotion, the more protection that sunscreen lotion will provide to the user. For example, a sunscreen lotion having an SPF rating of 2 provides very little protection from UV rays as compared to a sunscreen lotion having an SPF rating of 45. However, because sunscreen lotion also prevents tanning of the skin, all users do not wish to maximize UV ray protection by choosing a sunscreen lotion with the highest possible SPF rating. Thus, what is considered a desirable grade of sunscreen lotion to be applied to the skin varies from person to person.

Currently, when a person is at a beach, pool, or other outside area and they desire to utilize the protective effects of sunscreen lotion, they apply the sunscreen lotion to their skin by squeezing the lotion from the bottle into their hands. Once in their hands, the sunscreen lotion is applied to the remaining areas of their skin by manually rubbing it on the skin. This manual application has a number of drawbacks, the most significant which is the inability of the user to reach all areas of their skin. Even with the help of a second person, uneven distribution of the sunscreen lotion can occur, resulting in an uneven tan or unwanted exposure of certain areas of the skin to UV rays. Thus, improved methods and apparatus for applying sunscreen lotion to the skin are needed.

While a number of apparatus do exist that are capable of automatically applying sunscreen lotion to the skin of a user, these apparatus have a number of deficiencies and are not suited for convenient outdoor use. Examples of such apparatus are disclosed in U.S. Pat. No. 6,302,122, Parker et al.; U.S. Pat. No. 5,664,593, McClain; and U.S. Pat. No. 5,460,192, McClain. Typically, these existing apparatus are used to apply sun-tanning compositions to the body of a user and are located indoors within tanning spas. User access to these apparatus is regulated by an operator or other person working at the spa. Because these apparatus are located indoors, the circuitry and other susceptible components of these machines are not adequately protected from outdoor elements. Nor are these apparatus designed to provide the necessary privacy to a user in an outdoor public setting. As such, these apparatus can not be positioned outdoors at such places as on a beach or near a pool, the exact places where people most often experience the immediate need to apply sunscreen lotion. In addition to not being physically adapted for outdoor use, existing apparatus can not be placed on beaches and achieve economic success because access to existing apparatus can not be restricted without hiring extra personnel to monitor and operate the machines and collect revenue. Thus, a need still exists for an economically efficient machine that can effectively apply sunscreen lotion to a user in an outdoor setting.

SUMMARY OF THE INVENTION

These objects and others are met the present invention which in one aspect is a vending machine for dispensing sunscreen lotion comprising: means to accept payment from a user, means to store sunscreen lotion, and means to spray sunscreen lotion coupled to the means to store sunscreen lotion, the means to spray adapted to spray the user with the stored sunscreen after acceptance of payment. Preferably, the user obtains access to the machine through a door having a locking controller. In order to ensure that each user provides payment for the application of the sunscreen lotion, the locking means is electrically coupled to the means to accept payment. As such, the door unlocks only upon the means to receive payment receiving a payment from a user. In one embodiment, the locking means is coupled to a one-way lock that permits exit from inside the machine at all times. Using a one-way lock allows the user to freely exit the machine at any time and ensures that the door locks thereafter. Also preferably, the means to accept payment and the means to spray sunscreen lotion are coupled so that the means to spray sunscreen lotion can be activated only once for each payment received by the means to receive payment.

The machine can comprise user detection means adapted to detect location of the user within the machine. In this embodiment, the user detection means can be coupled to the means to spray sunscreen lotion. The user detection means can then be adapted so that upon detecting the user in a predetermined location in the machine, the means to spray sunscreen lotion are automatically activated. In this way, the sunscreen lotion can be applied to the user after payment has been made. Alternatively, the machine can comprise an activation means, wherein the activation means is coupled to the means to spray sunscreen lotion. Upon the activation means receiving an input from the user, the means to spray sunscreen lotion will be activated, applying sunscreen lotion to the user.

It is preferable that the means to store sunscreen lotion be adapted to store a plurality of grades of sunscreen lotion. In this embodiment, the machine will further comprise means for the user to select which grade of sunscreen lotion will be sprayed by the means to spray sunscreen lotion. Moreover, it is further preferable for the grades of sunscreen lotion to vary as to sun protection factor (SPF).

In yet another embodiment, the machine comprises means to store a disinfectant. In this embodiment, the means to spray sunscreen lotion is coupled with the means to store disinfectant which enables the means to spray sunscreen lotion to also be capable of spraying the disinfectant.

Preferably, the disinfectant will be sprayed to clean and sanitize the interior of the machine after the user has been sprayed with sunscreen lotion and has exited the machine. Whether the user has exited the machine or not can be determined by the user detection means discussed above.

It is also preferable for the machine to be adapted for outside use. In such an embodiment, the machine can comprise a drain that is fluidly connected to a reservoir. The drain and fluidly connected reservoir will drain any extra fluids that may remain in the machine after use. This allows the machine to be positioned anywhere, such as on the beach or near a pool. Additionally, the drain helps keep extra liquid from building up and forming slippery surfaces within the machine. In regards to preventing slipping, the machine can comprise a no-slip floor.

In order to further enable outside use, the machine can further comprise a water supply line that is fluidly connected to the means to spray sunscreen lotion on one end and a water supply on the other.

In the preferred embodiment, the machine will comprise both an application booth and a preparation booth. In this embodiment the means to spray sunscreen lotion will be located within the application booth which is adapted to fit the entire body of the user. The preparation booth will act as a staging area for the user in preparing for the application of the sunscreen lotion. As such, it will preferably have opaque walls and a means to hang a bathing suit.

In another aspect, the invention is a method of dispensing sunscreen lotion comprising: providing a machine which is adapted to receive and accept payment and store and spray sunscreen lotion; and spraying a user with the sunscreen lotion for a predetermined amount of time or volume of lotion upon a user providing payment to the machine.

In this aspect, it is preferable that the method further comprise the step of unlocking the machine so as to allow the user access to the machine after payment is received by the machine. Additionally, the step of spraying disinfectant in the machine after the user is sprayed with the sunscreen lotion can be performed.

DETAILED DESCRIPTION

Figure 1:
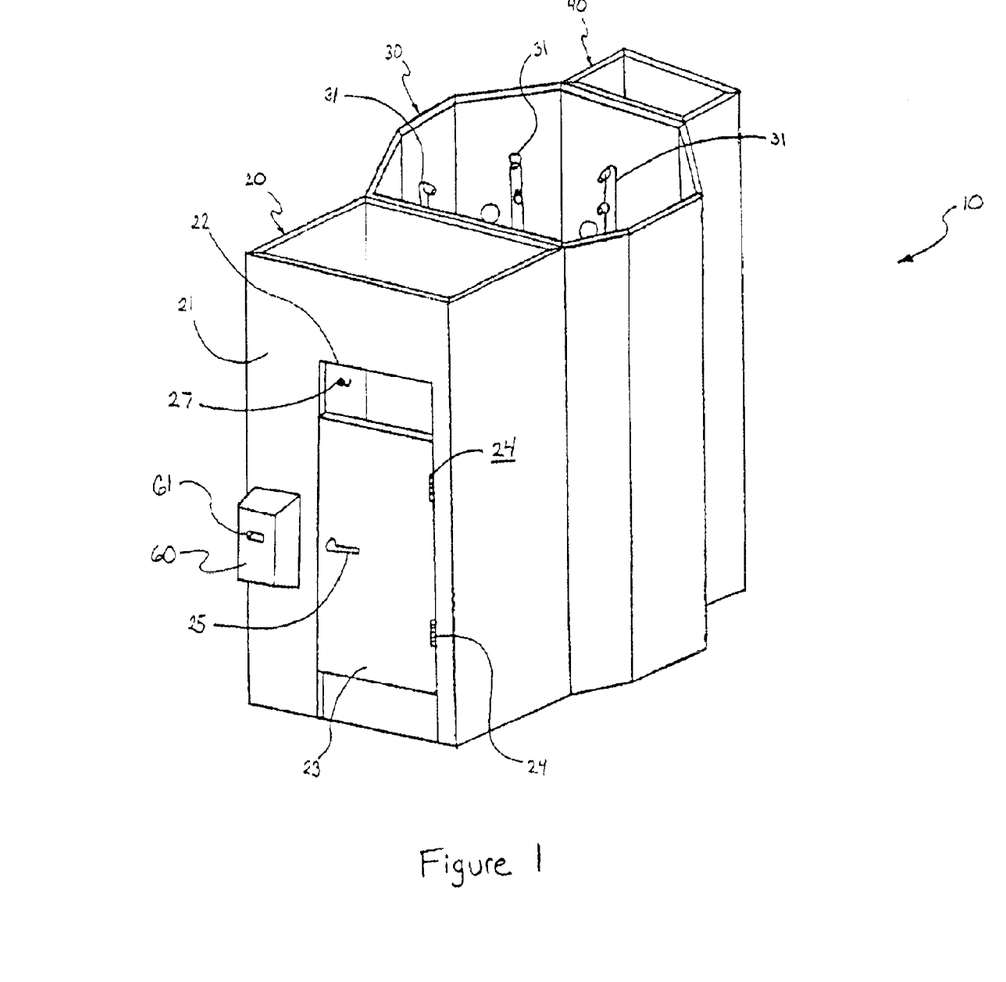
FIG. 1 is a perspective view of an embodiment of the present invention, a sunscreen application vending machine.
Figure 6:
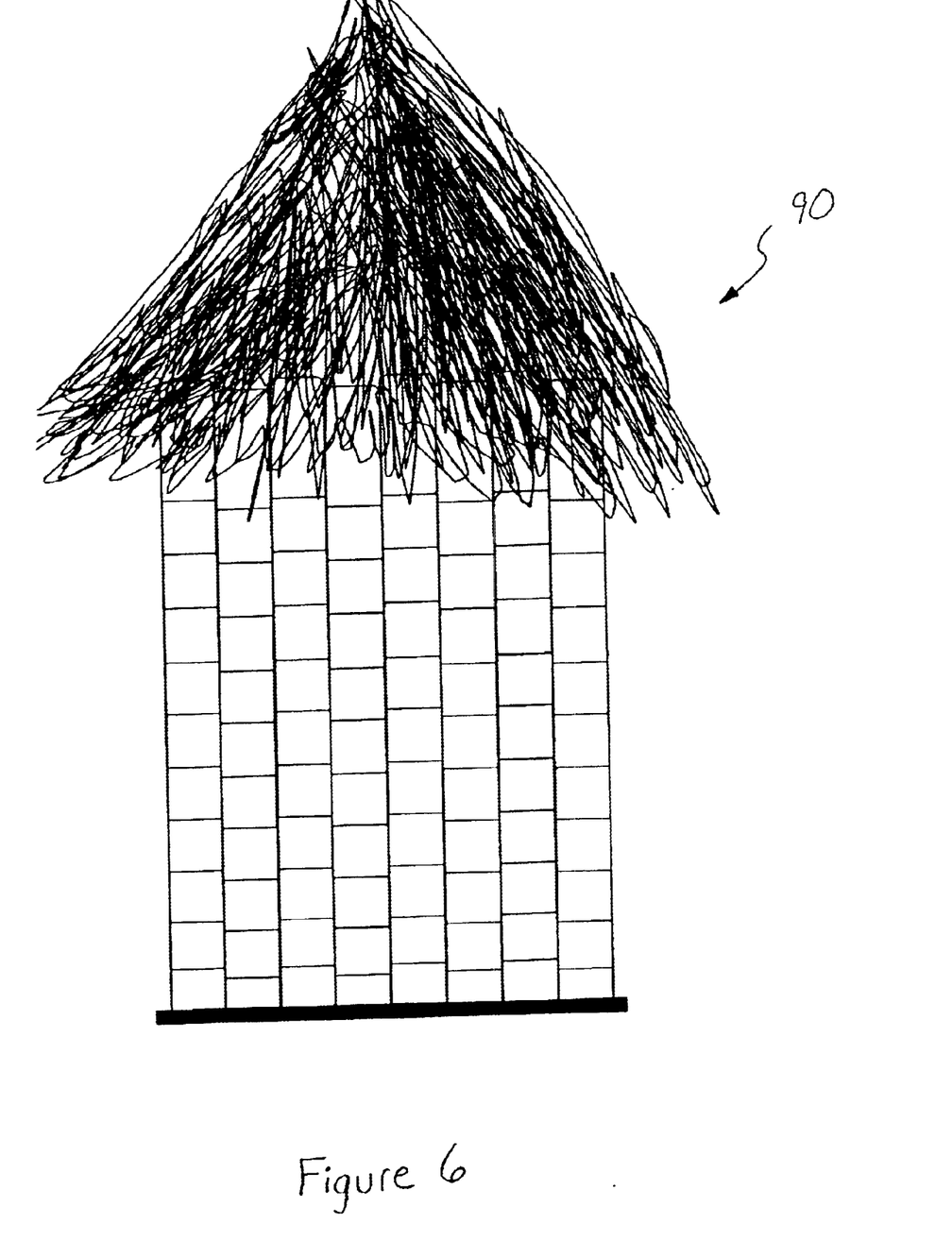
FIG. 6 is side view of a hut shell that can be sued to encompass the sunscreen application vending machine of FIG. 1 for aesthetic purposes.

Referring to FIG. 1, one embodiment of a sunscreen application vending machine 10 according to the present invention is illustrated. Sunscreen vending machine 10 comprises preparation booth 20, application booth 30, and equipment housing 40. Sunscreen vending machine 10 further comprises payment receiver 60. In order to better illustrate the interior elements of the invention, sunscreen vending machine 10 is illustrated without a roof over preparation booth 20, application booth 30, and equipment housing 40. However, in order for sunscreen vending machine 10 to be positioned outdoors, it is preferred that a roof be placed over preparation booth 20, application booth 30, and equipment housing 40. The roof can be weather-tight so that water can not enter any of the interior areas of the machine 10. If desired, the entire machine 10 can be enclosed by a hut 90 (FIG. 6) or other aesthetically desirable enclosure.

Figure 4:
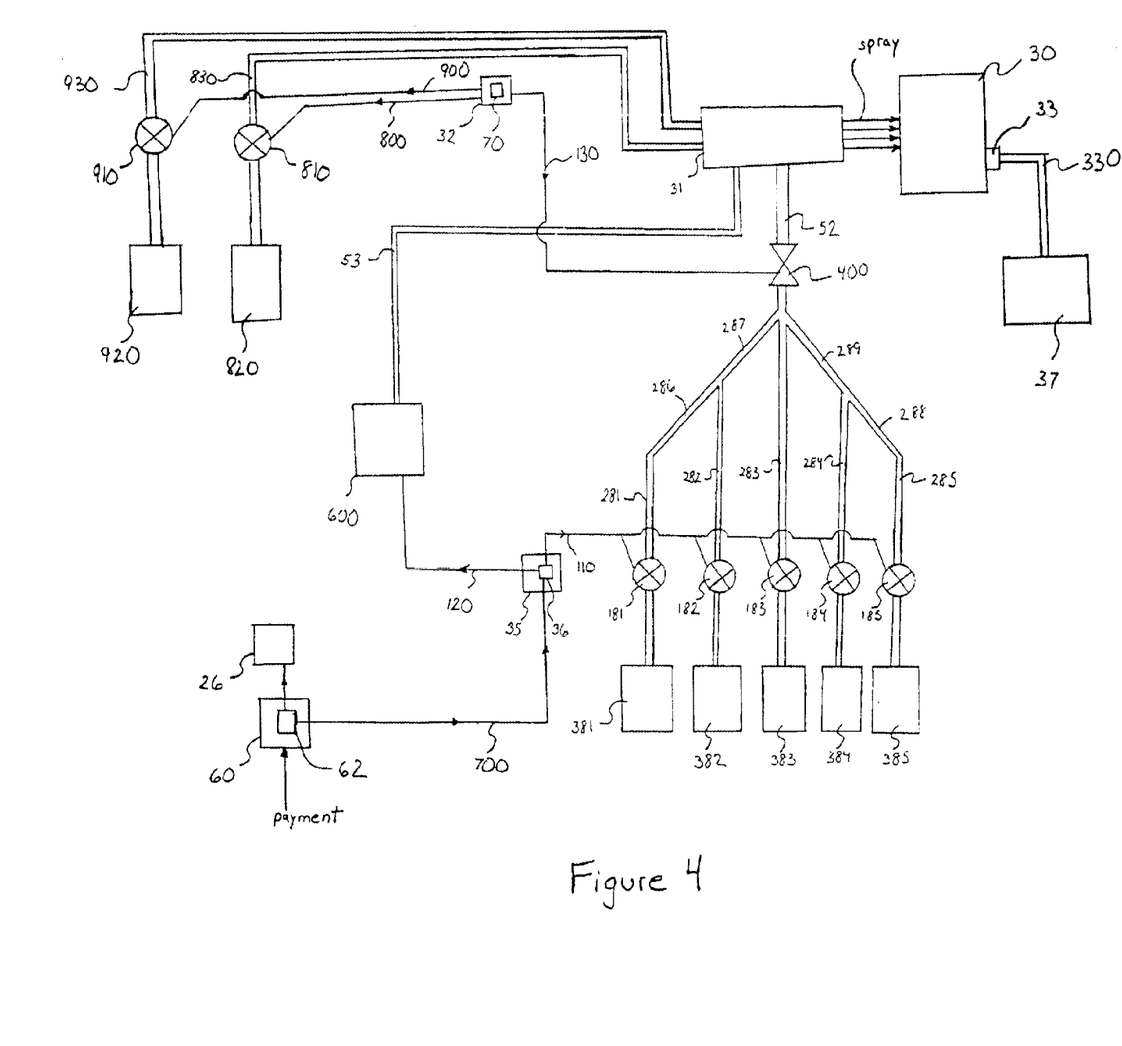
FIG. 4 is a schematic of the control system and equipment of the sunscreen application vending machine of FIG. 1.

Payment receiver 60 is mounted to front wall 21 of preparation booth 20. Payment receiver 60 comprises receiving slot 61 for receiving any type of conventional payment method, including coins, bills, credit cards, debit cards, or the like. Payment receiver 60 comprises a properly programmed processor 62 (FIG. 4). Processor 62 is properly configured and connected to other internal elements and circuitry of payment receiver 60 so as to be capable of determining the amount of money inputted by a user into receiving slot 61 or reading the amount of credit/debit on an inserted card. In the case of debit cards, processor 62 will deduct the required payment amount from the account and record the new balance on the magnetic strip. In the case of credit cards, payment receiver 60 ensures the required payment by connecting to the corresponding account through a communications line, such as a phone line or cable, and adding the required payment to the credit line of the card (as is done with conventional credit card machines). Once payment receiver 60 receives the required payment from a user, processor 62 sends the proper output signals to a variety of electrically connected devices. Any payment receiving system can be used, for example, those disclosed in U.S. Pat. No. 6,367,658, Kenney et al., and U.S. Pat. No. 6,367,696, Inamitsu et al.

Front wall 21 of preparation room comprises doorway 22. Doorway 22 provides users with access to the interior of sunscreen vending machine 10. Door 23 is mounted to doorway 22 by hinges 24. Door 23 comprises door knob 25 for opening and closing door 23. Door knob 23 is a "one-way locking door knob." When door 23 is closed, a user can not simply turn door knob 25 from the outside to gain entrance to the interior of sunscreen vending machine 10. However, door knob 23 does not lock from the interior and so if a user is within sunscreen vending machine 10, he or she can exit the machine by simply turning door knob 25 despite it being locked from the outside. Moreover, turning door knob 25 from the inside does not changed the locked status of the door knob from the exterior. Such door knobs and locking apparatus are very well known. Door 23 further comprises locking controller 26 (FIG. 4) within door 23 and coupled to door knob 25. Locking controller 26 controls when a user can gain access to the interior of sunscreen vending machine 10 by unlocking door knob 25 from the exterior upon receiving a proper signal from payment processor 62 (FIG. 4).

The walls of preparation booth 20 are preferably constructed of an opaque material. This provides a user with the privacy necessary if the user decides to remove his or her bathing suit before entering application booth 30 for the application of sunscreen lotion. Preparation booth 20 will further comprise hook 27 mounted to the one of the walls from which the user can hang his or her bathing suit. While a single book 27 is illustrated in FIG. 1, a multitude of apparatus can be used, including a clip, knob, peg, rack, or other suitable extrusion. Additionally, preparation booth 20 can further comprise a mirror, a bench, and disposable eye and head wear for the user.

Figure 2:
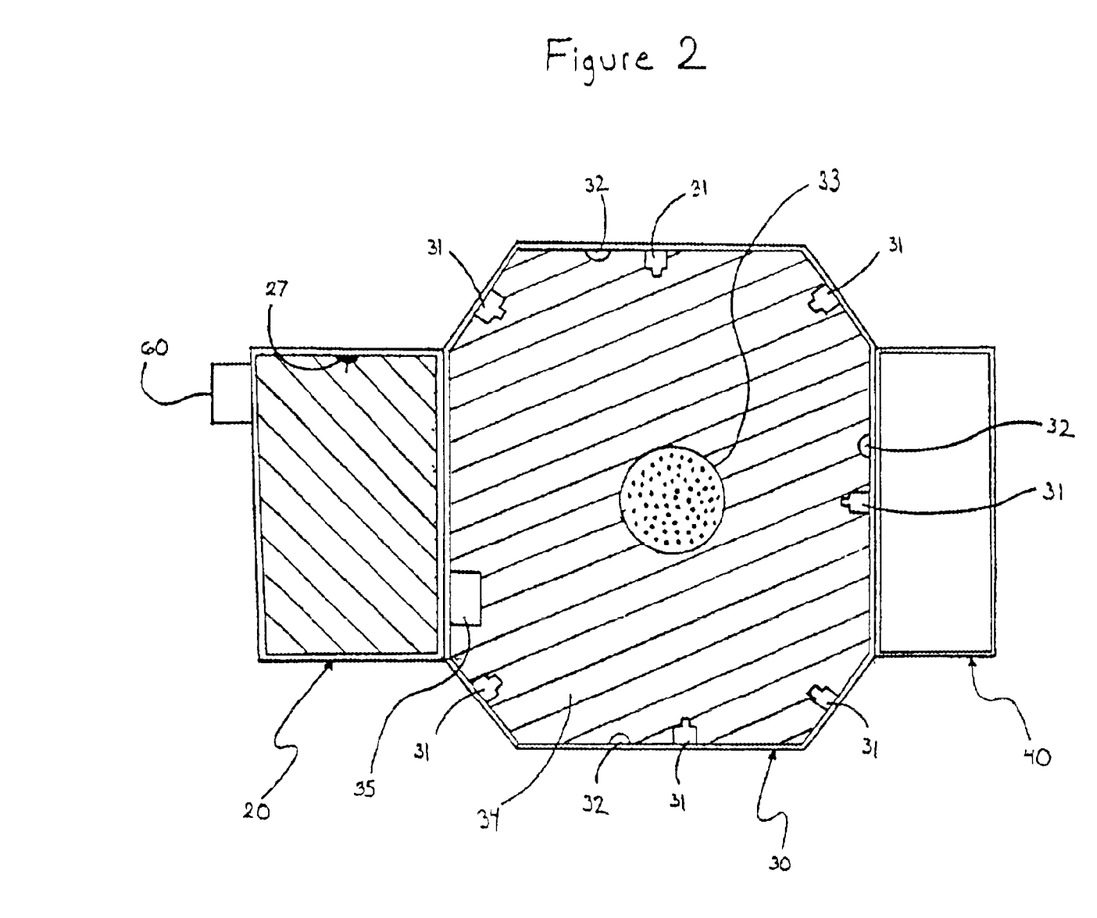
FIG. 2 is a top view of the sunscreen application vending machine of FIG. 1.

Referring to FIGS. 1 and 2, as illustrated, application booth 30 is a hexagonally shaped chamber. However, application booth 30 can be any shape, but it is preferred that its dimensions be designed so that a user can fit entirely therein and stand upright. For example, suitable length, width, and height dimensions could approximately be 90 inches, 48 inches, and 96 inches respectively.

Application booth 30 is adjacent to preparation booth 20 with a second doorway (not illustrated) leading from the interior of the preparation booth 20 to the interior of application booth 30. Second doorway 31 has a second door (not illustrated) extending the full length of second doorway 31. When the second door is closed, application booth 30 is an essentially closed chamber. The second door and doorway may or may not contain a door knob and coupled locking controller as described above.

Application booth 30 further comprises spray assemblies 31 mounted to the walls of application booth 30. Spray assemblies 31 are fluidly connected to the sunscreen lotion storage containers 41 (FIG. 4) that are located in equipment housing 40. Spray assemblies 31 spray atomized sunscreen lotion in an air current into application booth 30. Spray assemblies 31 are positioned around application chamber 30 so as to evenly coat the entire skin of a user who is standing in the center of the booth 30.

Application booth 30 also comprises sensors 32 located around the application booth 30. Sensors 32 can detect the presence and location of a user inside of application booth 30. Sensors 32 can be any type of conventional sensor that can detect objects and transmit appropriate signals to communicate with other devices, such as photo-optic, ultrasonic, and infrared sensors. As will be discussed in detail below, sensors 32 are electrically coupled to and can control the activation and deactivation of sprayer assemblies 31.

Additionally, application chamber comprises drain 33 and no-slip floor 34. Drain 33 is located in the approximate center of application chamber 30. Drain 33 is fluidly connected to a reservoir 37 (FIG. 4). As fluids, such as the sunscreen lotion or disinfectant, enter the application booth 30, excess fluid will build up. This excess fluid is removed from the booth 30 by drain 33. Because the excess fluid may contain chemicals that are not environmentally safe to be dumped, the drain can be fluidly connected to a reservoir 37 (FIG. 4) from which the fluids can be removed and/or treated. Flow of the excess fluid into drain 33 is facilitated by the pitch of the floor 34 (indicated by the striped lines). Preferably, floor 34 is constructed so as to be a no-slip floor (i.e., slip-resistant). Slip resistant floors are very well known in the art and generally consist of raised portions and channels for carrying away fluid located between the raised portions. An example of a slip-resistant floor is disclosed in U.S. Pat. No. 5,815,995, Adam.

Finally, application chamber 30 comprises user control panel 35. User control panel 35 is mounted to the wall of application chamber 30.

Figure 3:
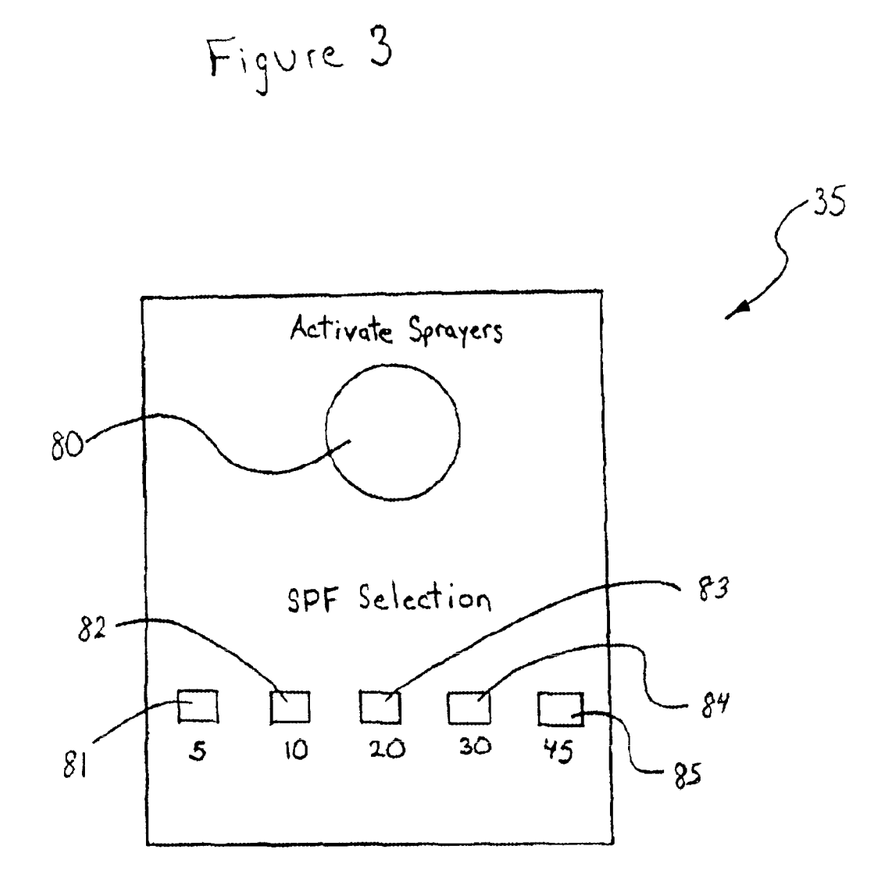
FIG. 3 is a front view of a user control panel that can be sued to control some of the functions of the sunscreen application vending machine of FIG. 1.

Referring to FIG. 3, user control panel 35 contains a variety of buttons 80–85. In the illustrated embodiment, a user can select which SPF grade of sunscreen lotion he or she wishes to have applied by sprayer assemblies 31 by pressing the corresponding button 81–85 on control panel 35. As will be discussed in reference to FIG. 4 below, control panel 35 is coupled to sprayer assemblies 31 and the pumps that control which SPF grade will be sprayed therethrough. Additionally, control panel 35 will comprise activation button 80 in those embodiments of the sunscreen application vending machine 10 that do not have sensors 31 that will automatically start spraying sunscreen lotion upon the user being detected in a predetermined position and an SPF grade of sunscreen lotion being chosen as discussed above. Upon a user pressing activation button 80, sprayer assemblies 31 will be activated, spraying the user with the selected SPF grade of sunscreen lotion.

Referring back to FIG. 1., equipment housing 40 holds the necessary equipment, circuitry, and supplies needed to operate sunscreen application vending machine 10. For example, equipment housing 40 holds the pumps, containers of sunscreen lotion with various SPF grades; disinfectant liquid, flow meters, wiring, and the like.

Figure 5:
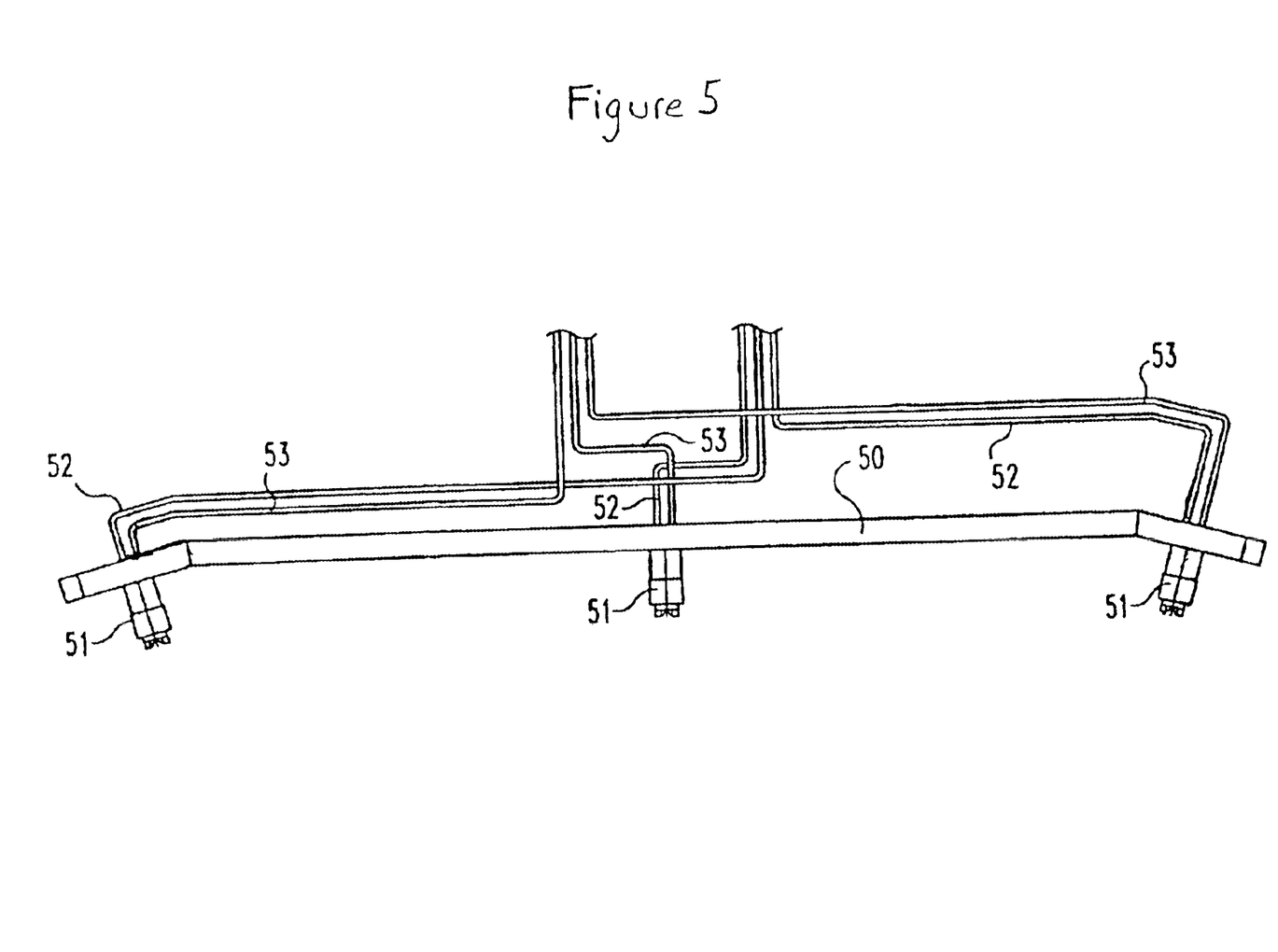
FIG. 5 is a side view of an embodiment of sprayer assembly used in the sunscreen application vending machine of FIG. 1.

Referring now to FIG. 5, an example of a suitable spraying assembly 31 is shown. While the illustration shows one embodiment of a spraying system, suitable spraying mechanisms and are very well known in the art. For examples of such sprayers, see U.S. Pat. No. 6,302,122, Parker et al.; U.S. Pat. No. 5,664,593, McClain; and U.S. Pat. No. 5,460,192, McClain. Spraying assembly 31 comprises an arm 50 having three active nozzles 51. One spray nozzle 51 is on the central portion of arm 50 and one spray nozzle 51 is on each of the two outer portions of arm 50. Each spray nozzle 51, when activated sprays in a direction towards a certain location in the application booth 30, said location being the location for positioning a user during use, also referred to as the predetermined location.

In operation, the plurality of spray nozzles 51 produce a spray optimized to provide a relatively even coating on the skin of a user, with substantially no streaking or dripping. This can be accomplished by regulating the spray patterns and spray direction geometries of the nozzles, as well as the average droplet particle size, the nozzle liquid and air feed pressures, and the viscosity of the sunscreen lotion. One specific example of a suitable nozzle and operating conditions, without limitation, is the external mix, flat spray, air atomizing 1/8J with a SUE 18B Spray set-up available from Spraying Systems Co., Wheaton Ill., operating at a liquid pressure of about 5 to about 20 psi (about 35–140 kPa), preferably about 10 psi (about 70 kPa) and air pressures in the range of about 15 to about 30 psi (about 100 to about 200 kPa).

A predetermined location within the booth is provided for a user to stand during a sunscreen lotion application operation according to the present invention. It is generally convenient for the location to be in the central portion of the application booth 40 though alternatives may be suitable for design considerations, as for example, the back, side or front of the booth relative to the arm. In one embodiment, the predetermined location is in front of the spray nozzles at a horizontal distance of between about 25 cm and 60 cm, measuring to the surface of the user's body closest to the nozzles. Greater or lesser distances can be used by adjusting the nozzle liquid and air feed pressures accordingly, as for example by increasing the feed pressures for greater distances. Greater distances, however, may lead to greater spray pattern dispersion and more combining of spray droplets, resulting in a sub-population of less desirable large droplets, which may drip or streak after deposition on the skin or result in an uneven coating.

In the illustrated embodiment, arm 50 is a manifold. The manifold 50 is a two compartment bar providing pressurized feed of sunscreen lotion through sunscreen lotion feed line 52 into one compartment, and pressurized feed of air through compressed air feed line 53 into the second compartment. In this manner, each nozzle 51 receives equivalent feeds of air and liquid which is then atomized into a spray in the nozzle 51. Optionally, manifold 50 may be fitted with disinfectant feed line and a water feed line to spray application booth 30 in a cleaning and sanitizing step.

FIG. 4 is a schematic representation of the control system and equipment used to make sunscreen application vending machine 10 works. In order to use sunscreen application vending machine 10, a user must approach the machine 10 and deposit the required payment in payment receiver 60 as described above. Upon detecting receipt of adequate payment into payment receiver 60, payment receiver processor 62 sends the appropriate output signal 100 to locking controller 26. Payment receiver processor can be any type of properly programmed CPU chip, such as those manufactured by Intel. Upon receiving output signal 100, locking controller 26 unlocks door knob 25 so the user can access the interior of preparation room 20. Locking controllers that are capable of locking and unlocking doors upon receiving an such inputs are well known in the art. See for example U.S. Pat. No. 6,365,986, Nonome, and U.S. Pat. No. 6,382,003, Watanuki et al.

Additionally, upon detecting receipt of adequate payment into payment receiver 60, payment receiver processor 62 sends output signal 700 to panel processor 36 within user control panel 35. Before receiving output signal 700, panel processor 36 and user control panel 35 are in a deactivated state and cannot be receive input directly form a user within application booth 20. However, once output signal 700 is received, panel processor 36 and user control panel 35 are "awakened" and can perform the function described below.

Once the user is within preparation booth 20, door 23 closes behind the user, automatically locking from the outside. In order to ensure that door 23 closes, hinges 24 can be spring loaded. The user will then prepare for the application of the sunscreen lotion by taking off his or her bathing suit and wearing eye and head gear if desired. The user then enters application booth 30. Upon entering application booth 30, the user will select which SPF grade of sunscreen lotion that he or she desire to have applied to their body by pressing the corresponding button 81–85 on user control panel 35. User control panel 35 comprises properly programmed control panel processor 36 which receives the inputted SPF grade selection from the user. In response to receiving this input, panel processor 36 sends signal 110 to the appropriate pump 181–185. Pumps 181–185 are operably coupled to corresponding fluid lines 281–285 which in turn are fluidly connected to corresponding sunscreen lotion tanks 381–385. Sunscreen lotion tanks 381–385 are located within equipment housing 40 and each contain a different SPF grade of sunscreen lotion. Assuming that the user presses SPF selection button 83, which corresponds to sunscreen lotion having an SPF of 20, panel processor 36 send output signal 110 to pump 183, activating pump 183. Pump 83 then pumps the SPF 20 sunscreen lotion from tank 383 through fluid line 283 until the sunscreen lotion reaches flow valve 400. At this point flow valve 400 is closed and as such, the sunscreen lotion can not flow into sunscreen feed line 52 as of yet. In order to avoid mixing of the various SPF grades, single-direction flow valves must be strategically placed on fluid lines 281–289.

In addition to sending output signal 110, panel controller also sends appropriate output signal 120 to air compressor 600, thus activating air compressor 600. Once activated, air compressor 600 forces air to flow through compressed air feed line 53 and into spraying assemblies 31 and out of nozzles 51 as described in relation to FIG. 5 above.

Once the user has selected the desired SPF grade of sunscreen lotion to be applied, the user positions himself in the center of application booth 30 (i.e., the predetermined location) Upon moving into the predetermined location, sensors 32 detect the user's presence therein and sensor processor 70 (which is located in the sensors 32) sends output signal 130 to flow valve 400. Upon receiving output signal 130, valve 130 is opened to allow an appropriate volume of the SPF 20 sunscreen lotion being pumped by pump 183 to flow therethrough and into sunscreen lotion feed line 52 and eventually sprayer assemblies 31. Spray assemblies 31 then spray the sunscreen lotion mist onto the user as described above with respect to FIG. 5. Alternatively, in an embodiment that does not use sensors 32, panel processor 36 will send output signal 130 to flow valve 400 upon a user pressing the activate sprayer button 80.

After a predetermined period of time (or volume flow of sunscreen lotion), panel processor 36 sends output signals to both air compressor 600 and pump 183 to terminate operation, thereby discontinuing spray of sunscreen lotion mist. At this point, user control panel 35 and panel controller 36 go into a deactivated state and cannot be activated again until payment processor sends another output signal 700 confirming payment.

Upon the user leaving application booth 30, sensors 32 detect the absence of the user and sensor processor 70 sends output signals 800 and 900 to disinfectant pump 810 and water pump 910 respectively, activating pumps 810 and 910. Simultaneously, a signal 130 is sent to flow valve 400, causing flow valve 400 to once again be closed. Pump 810 is fluidly connected to disinfectant tank 820 which holds a disinfectant solution. Water pump 910 is fluidly connected to water supply tank 920. Upon being activated, pumps 810 and 910 pump disinfectant solution and water through disinfectant feed line 830 and water feed line 930 respectively. The water and disinfectant solution are then fed into sprayer assemblies 31. Sprayer assemblies 31 then spray the disinfectant-water solution over the interior of the application booth 30, cleaning and sanitizing the entire booth 30. After a predetermined period of time, sensor processor 70 sends an appropriate signal to pumps 810 and 910 to terminate operation. Optionally, water pump 910 can be allowed to operate for bit longer in order to clean the feed lines and sprayers of any chemicals.

All excess fluids that enter application booth 20 flow into drain 33, through drain lines 330, and eventually into reservoir 37. Once inside reservoir 37, these excess fluids can be properly disposed of or treated.

The foregoing discussion discloses and describes merely exemplary embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

What is claimed is:

1. A vending machine for dispensing sunscreen lotion comprising:
   means to accept payment from a user,
   means to store sunscreen lotion, and
   means to spray the user with the stored sunscreen lotion after acceptance of payment
   wherein the means to store sunscreen lotion is adapted to store a plurality of grades of sunscreen lotion, the machine further comprising means for the user to select which grade of sunscreen lotion will be sprayed by the means to spray.

2. The machine of claim 1 comprising a door that provides access to the machine, the door comprising a locking controller coupled to the means to accept payment, the locking controller adapted to unlock the door to allow entrance upon the means to receive payment receiving payment from a user.

3. The machine of claim 2 wherein the locking controller is coupled to a means comprises a one-way lock that permits exit from inside the machine.

4. The machine of claim 1 wherein the means to accept payment is coupled to the means to spray so that the means to spray can be activated only once for each payment received by the means to receive payment.

5. The machine of claim 1 comprising a drain fluidly connected to a reservoir.

6. The machine of claim 1 comprising user detection means, the user detection means adapted to detect location of the user within the machine.

7. The machine of claim 6 wherein the user detection means is coupled to the means to spray and adapted to activate the means to spray upon a user being detected in a predetermined location within the machine.

8. The machine of claim 1 comprising means to store a disinfectant, wherein the means to spray is coupled to the means to store disinfectant and adapted to spray the disinfectant.

9. The machine of claim 1 comprising a no-slip floor.

10. The machine of claim 1 comprising activation means, the activation means adapted to activate the means to spray upon receiving an input from the user.

11. The machine of claim 1 wherein the grades of sunscreen lotion vary as to sun protection factor (SPF).

12. The machine of claim 1 wherein the machine is adapted for outside use.

13. The machine of claim 1 comprising a water supply fluidly connected to the means to spray.

14. The machine of claim 1 wherein the means to spray are located within an application booth adapted to fit the entire body of the user.

15. The machine of claim 14 comprising a preparation booth connected to the application booth.

16. The machine of claim 15 wherein the preparation booth comprises opaque walls and means to hang a bathing suit.

17. A method of dispensing sunscreen lotion comprising:
providing a machine which is adapted to receive and accept payment and store and spray sunscreen lotion;
spraying a user with the sunscreen lotion for a predetermined amount of time or volume of lotion upon a user providing payment to the machine;
storing a plurality of grades of sunscreen lotion; and
providing means for the user to select which grade of sunscreen lotion will be sprayed by the means to spray.

18. The method of claim 17 further comprising unlocking the machine so as to allow the user access to the machine after payment is received by the machine.

19. The method of claim 17 further comprising spraying disinfectant in the machine after the user is sprayed with the sunscreen lotion.

* * * * *